US009157860B2

(12) United States Patent
Boege (10) Patent No.: US 9,157,860 B2
(45) Date of Patent: Oct. 13, 2015

(54) ACHROMATIC LENS ARRAY

(75) Inventor: Steven J. Boege, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1025 days.

(21) Appl. No.: 11/225,968

(22) Filed: Sep. 13, 2005

(65) Prior Publication Data

US 2006/0006344 A1 Jan. 12, 2006

Related U.S. Application Data

(63) Continuation-in-part of application No. 11/096,341, filed on Mar. 31, 2005, now Pat. No. 7,407,798, which is a continuation-in-part of application No. 10/146,066, filed on May 16, 2002, now Pat. No. 6,982,166.

(51) Int. Cl.
*C12M 1/34* (2006.01)
*G01N 21/00* (2006.01)
*G01N 21/64* (2006.01)
*G01N 21/66* (2006.01)
*G01J 3/30* (2006.01)
*C12M 3/00* (2006.01)
*G01J 3/02* (2006.01)

(52) U.S. Cl.
CPC ........ *G01N 21/6452* (2013.01); *G01N 21/6486* (2013.01); *G01J 3/0208* (2013.01); *G01N 2021/6478* (2013.01)

(58) Field of Classification Search
USPC ............. 435/288.7; 356/317, 318; 422/82.05, 422/82.08
See application file for complete search history.

(56) References Cited

U.S. PATENT DOCUMENTS

| 5,096,807 A | 3/1992 | Leaback |
| 5,234,665 A | 8/1993 | Ohta et al. |
| 5,315,375 A | 5/1994 | Allen |
| 5,682,232 A | 10/1997 | Tajima et al. |

(Continued)

FOREIGN PATENT DOCUMENTS

| DE | 19748211 | 5/1999 |
| DE | 20321717 | 4/2009 |

(Continued)

OTHER PUBLICATIONS

Yasuhiro Tanaka et al., Diffractive-Refractive Achromatic Lens for Optical Disc System by Glass Molding, 1998, Optical Review, vol. 5, No. 6, pp. 334-339.*

(Continued)

*Primary Examiner* — Nathan Bowers
*Assistant Examiner* — Lydia Edwards (57) ABSTRACT

A luminescence detection system may include an excitation light source, a single element achromat, and a detector. The single element achromat may be configured to regulate the excitation light from the light source and direct the regulated light to a target, and the detector may be configured to detect luminescence generated by the target. The single element achromat may be configured to regulate the emission light from the target and direct the regulated light to a detector, and the excitation light source may be configured to direct the excitation light to the target. The single element achromat may be configured to regulate both the excitation light from the light source and the emission light from the target and direct the regulated light to, respectively, the target and a detector.

16 Claims, 5 Drawing Sheets

(56) References Cited

U.S. PATENT DOCUMENTS

| | | | |
|---|---|---|---|
| 5,734,496 A | 3/1998 | Beach | |
| 5,774,214 A | 6/1998 | Prettyjohns et al. | |
| 5,780,857 A | 7/1998 | Harju et al. | |
| 5,892,577 A | 4/1999 | Gordon | |
| 5,928,907 A | 7/1999 | Woudenberg et al. | |
| 5,961,926 A | 10/1999 | Kolb et al. | |
| 5,993,746 A | 11/1999 | Priha et al. | |
| 6,008,892 A | 12/1999 | Kain et al. | |
| 6,015,674 A | 1/2000 | Woudenberg et al. | |
| 6,024,920 A | 2/2000 | Cunanan | |
| 6,027,695 A | 2/2000 | Oldenburg et al. | |
| 6,033,605 A | 3/2000 | Szlosek | |
| 6,130,745 A | 10/2000 | Manian | |
| 6,232,114 B1 | 5/2001 | Coassin et al. | |
| 6,238,911 B1* | 5/2001 | Kasahara | 435/288.4 |
| 6,246,525 B1 | 6/2001 | Ikami | |
| 6,256,088 B1 | 7/2001 | Gordon | |
| 6,258,326 B1 | 7/2001 | Modlin | |
| 6,262,846 B1* | 7/2001 | Nakai | 359/576 |
| 6,271,972 B1 | 8/2001 | Kedar et al. | |
| 6,272,939 B1 | 8/2001 | Frye et al. | |
| 6,278,560 B1* | 8/2001 | Hendriks | 359/738 |
| 6,280,960 B1 | 8/2001 | Carr | |
| 6,304,378 B1 | 10/2001 | Clausen | |
| 6,330,017 B1 | 12/2001 | Suzuki et al. | |
| 6,366,405 B2 | 4/2002 | Abe | |
| 6,381,072 B1 | 4/2002 | Burger | |
| 6,388,788 B1 | 5/2002 | Harris | |
| 6,399,952 B1 | 6/2002 | Maher et al. | |
| 6,437,345 B1 | 8/2002 | Bruno-Raimondi | |
| 6,473,239 B1* | 10/2002 | Volcker et al. | 359/624 |
| 6,514,750 B2 | 2/2003 | Bordenkircher et al. | |
| 6,563,581 B1* | 5/2003 | Oldham et al. | 356/317 |
| 6,750,457 B2 | 6/2004 | Heffelfinger et al. | |
| 6,818,437 B1* | 11/2004 | Gambini et al. | 435/288.7 |
| 6,942,836 B2 | 9/2005 | Freudenthal et al. | |
| 7,407,798 B2 | 8/2008 | Oldham et al. | |
| 2002/0030894 A1* | 3/2002 | Volcker et al. | 359/619 |
| 2002/0168665 A1 | 11/2002 | Okawa | |
| 2003/0044967 A1* | 3/2003 | Heffelfinger et al. | 435/287.2 |

FOREIGN PATENT DOCUMENTS

| | | |
|---|---|---|
| EP | 0395156 | 10/1990 |
| EP | 0545284 | 6/1993 |
| EP | 0814300 | 12/1997 |
| EP | 2053429 | 4/2009 |
| GB | 2187567 | 9/1987 |
| JP | 02210310 | 8/1990 |
| JP | 02280707 | 11/1990 |
| JP | 11500232 | 1/1999 |
| JP | 11202105 | 7/1999 |
| JP | 2001/166254 | 6/2001 |
| JP | 2002/507762 | 3/2002 |
| JP | 2002/527743 | 8/2002 |
| JP | 2009/222506 | 10/2009 |
| WO | WO95/30139 | 11/1995 |
| WO | WO-97/36681 | 10/1997 |
| WO | WO-98/10314 | 3/1998 |
| WO | WO98/57151 | 12/1998 |
| WO | WO-99/60381 | 11/1999 |
| WO | WO00/22417 | 4/2000 |
| WO | WO-00/22417 | 4/2000 |
| WO | WO-00/25922 | 5/2000 |
| WO | WO00/58715 | 10/2000 |
| WO | WO-00/65325 | 11/2000 |
| WO | WO-01/28684 | 4/2001 |
| WO | WO-01/35079 | 5/2001 |
| WO | WO-01/35097 | 5/2001 |

OTHER PUBLICATIONS

S. Keren et al., Three-Dimensional Optical Metrology With Color-Coded Extended Depth of Focus, 1999, Optics Letters, vol. 24, No. 7, pp. 439-441.*

John Canning et al., Silica-Based Fibre Fresnel Lens, 2001, Optics Communcations vol. 199, pp. 375-381.*

Robert W. Cohn, et al., "Fully Complex Diffractive Optics by Means of Patterned Diffuser Arrays: Encoding concept and Implications for Fabrication," *J. Opt. Soc. Am. A*, May 1997, 1110-1123, vol. 14, No. 5.

Yasuhiro Tanaka, et al., "Diffractive-Refractive Achromatic Lens for Optical Disk System by Glass Molding," *Optical Review*, 1998, 334-339, vol. 5, No. 6.

Extended European Search Report of the European Patent Office for application No. 09152555.0-2217, dated Mar. 27, 2009.

U.S. Appl. No. 11/225,934 Response to Sep. 15, 2009 Final Office Action filed Mar. 11, 2010.

U.S. Appl. No. 11/225,934, "Office Action Mailed Apr. 12, 2010", 13 pgs.

U.S. Appl. No. 11/225,968, "Response to Aug. 25, 2009 Office Action filed on Feb. 24, 2010", 5 pgs.

2004-505751, "Office Action Inquiry mailed on Sep. 30, 2009", 3 pgs.

2004-505751, "Office Action mailed Jan. 15, 2010", 5 pgs.

2004-505751, "Office Action mailed Nov. 30, 2009", 31 pgs.

2004-505751, "Response to Sep. 30, 2009 Office Action filed on Oct. 8, 2009", 7 pgs.

2004-505751, "Response to OA mailed Nov. 30, 2009 filed on Dec. 17, 2009", 10 pgs.

2007219091, "Office Action Mailed Jun. 15, 2010", 4 pgs.

PCT/US03/15586 "International Search Report dated Aug. 18, 2003", 3 pgs.

EP09152555.0, Annex to the European Search Report mailed Mar. 20, 2009, 1 pg.

EP09152555.0, European Search Report mailed Mar. 20, 2009, 1 pg.

EP10183609.6, Extended European Search Report mailed Feb. 23, 2011, 9 pgs.

U.S. Appl. No. 11/225,934, Non-Final Office Action mailed Dec. 10, 2008, 12 pgs.

U.S. Appl. No. 11/225,934, Final Office Action mailed Sep. 15, 2009, 12 pgs.

U.S. Appl. No. 11/225,934, Non-Final Office Action mailed Apr. 12, 2010, 12 pgs.

U.S. Appl. No. 11/225,934, Final Office Action mailed Oct. 21, 2010, 12 pgs.

U.S. Appl. No. 11/225,934, Response to Dec. 10, 2008 Office Action filed Jun. 9, 2009, 5 pgs.

U.S. Appl. No. 11/225,934, Response to Sep. 15, 2009 Final Office Action filed Mar. 11, 2010, 5 pgs.

U.S. Appl. No. 11/225,934, Response to Apr. 12, 2010 Office Action filed Sep. 13, 2010, 7 pgs.

U.S. Appl. No. 11/225,934, Response to Oct. 21, 2010 Office Action filed Mar. 21, 2011, 9 pgs.

* cited by examiner

ACHROMATIC LENS ARRAY

CROSS-REFERENCE TO RELATED APPLICATION

The present application is a continuation-in-part of U.S. patent application Ser. No. 11/096,341, filed Mar. 31, 2005, and patent application Ser. No. 10/146,066, filed May 16, 2002, now U.S. Pat. No. 6,982,166, which is incorporated herein by reference in its entirety.

FIELD

The present invention relates to an optical system for focusing light onto or collecting light from one or more samples in a system for biological testing. In one aspect, the invention relates to a lens assembly having the functions of collimating and focusing light onto one or more samples integrated into the lens assembly. In another aspect, the invention relates to a lens assembly having the functions of collimating and focusing light from one or more samples integrated into the lens assembly.

BACKGROUND

Biological testing has become an important tool in detecting and monitoring diseases. In the biological testing field, thermal cycling is used to amplify nucleic acids by, for example, performing PCR and other reactions. PCR in particular has become a valuable research tool with applications such as cloning, analysis of genetic expression, DNA sequencing, and drug discovery.

Recent developments in the field have spurred growth in the number of tests that are performed. One method for increasing the throughput of such biological testing is to provide real-time detection capability during thermal cycling. Real-time detection increases the efficiency of the biological testing because the characteristics of the samples can be detected while the sample well tray remains positioned in the thermal cycling device.

In a real-time detection system, testing may be performed on multiple samples during a cycle of the testing device. With this type of system, light may be emitted from a light source to be reflected off of the biological sample(s) and ultimately may be detected or collected by a light detecting device such as a camera or CCD, for example. To assist with focusing the light into and directing the light out of the samples toward detecting device, one or more lenses may be provided.

One of the drawbacks of conventional devices utilizing lens assemblies in conjunction with multiple sample testing devices is the complexity of the lens(es). It may often be desirable to have a lens for collimating light so that it may be properly aligned with a row or column of sample wells in a sample well tray. To further enhance the testing process, an additional lens assembly may be provided for focusing light more precisely within each of the sample wells. These focusing lens assemblies often may comprise a plurality of non-integral components, resulting in a bulky structure.

Another drawback of conventional devices is chromatic aberration. Some conventional instruments comprise light sources emitting light having one or more excitation wavelengths and samples emitting light at one or more emission wavelengths. Optical systems direct excitation light from sources to samples and/or from samples to detectors. When these systems are not corrected for chromatic aberration, vignetting and system throughput become functions of wavelength. When the systems are corrected for chromatic aberration, wavelength-dependent response variations may be substantially reduced.

Some conventional sample testing devices utilize two or more bonded lens elements that serve to collect and focus light. Such devices may have a less bulky structure, but the use of bonded elements of materials with different dispersions may result in spherical and/or chromatic aberration of the light. Some conventional refractive achromats may correct both spherical and chromatic aberrations, but typically require the use of glass and more costly fabrication.

Accordingly, it may be desirable to provide a sample testing device having a diffractive/refractive hybrid lens that reduces spherical and/or chromatic aberration of light. It may be desirable to manufacture the diffractive/refractive hybrid from a polymer with a single-step process, thus saving material and manufacturing costs.

SUMMARY

In accordance with various aspects of the invention, a luminescence detection system may comprise a light source configured to illuminate a target, a detector configured to detect target luminescence, and a single element achromat configured to regulate at least one of light from the light source and luminescence from the target.

In accordance with various aspects, a lens assembly may comprise a single element achromat configured to regulate at least one of light illuminating a target and target luminescence.

According to various aspects of the invention, the single element achromat may comprise a single surface comprising at least one refractive feature and at least one diffractive feature. The at least one diffractive feature may be configured to minimize chromatic aberration of at least one of the light from the light source and the luminescence from the target.

According to some aspects, the at least one refractive feature may comprise a spherical feature or an aspheric feature configured to minimize spherical aberration of at least one of the light from the light source and the luminescence from the target.

In accordance with various aspects, the single element achromat may comprise a refractive surface and a diffractive surface. The diffractive surface may be configured to minimize chromatic aberration of at least one of the light from the light source and the luminescence from the target.

In accordance with some aspects, the refractive surface may comprise a spherical surface or an aspheric refractive surface configured to minimize spherical aberration of at least one of the light from the light source and the luminescence from the target.

According to various aspects, a method of luminescence detection may comprise Illuminating a sample, detecting sample luminescence, and passing at least one of light illuminating the sample and the sample luminescence through a single element achromat.

In accordance with some aspects, at least one of light illuminating the sample and the sample luminescence may be passed through a single surface comprising at least one refractive feature and at least one diffractive feature. The diffractive feature may be configured to minimize chromatic aberration of at least one of the illuminating light and the target luminescence.

In accordance with various aspects, at least one of light illuminating the sample and the sample luminescence may be passed through a refractive surface and a diffractive surface.

The diffractive surface may be configured to minimize chromatic aberration of at least one of the illuminating light and the target luminescence.

According to various aspects, an optical detection system for a thermal cycling device may comprise at least one light source configured to illuminate at least one of a plurality of samples, a light detection device configured to detect luminescence from at least one of a plurality of biological samples, and a lens. The lens may have first and second surfaces, wherein the second surface faces a direction opposite to that of the first surface. The first surface may be configured to collimate light, and the second surface may comprise a matrix of lenses. The matrix may comprise a plurality of focusing lens portions configured to direct light into each of the plurality of biological samples. Each focusing lens portion may comprise at least one refractive feature and at least one diffractive feature. The diffractive feature may be configured to minimize chromatic aberration of at least one of light from the light source and the luminescence from the target.

BRIEF DESCRIPTION OF THE DRAWINGS

The accompanying drawings, which are incorporated in and constitute a part of this specification, illustrate at least one exemplary embodiment of the invention. In the drawings.

DESCRIPTION OF THE VARIOUS EMBODIMENTS

Reference will now be made in detail to exemplary embodiments of the invention, examples of which are illustrated in the accompanying drawings. Wherever possible, the same reference numbers are used in the drawings and the description to refer to the same or like parts, and the same reference numbers with alphabetical suffixes or numerical prefixes are used to refer to similar parts.

In accordance with certain embodiments, a biological testing device is provided. In one aspect, the biological testing device can perform nucleic acid amplification. In certain embodiments, the biological testing device includes a light source, a light detection device, and a lens. In various embodiments, the biological testing device can also include a sample block, a heated cover, a sample well tray, a seal for covering openings of the sample wells in the sample well tray, a light refractor, a light reflector, and/or a filter, among other components.

Figure 1:
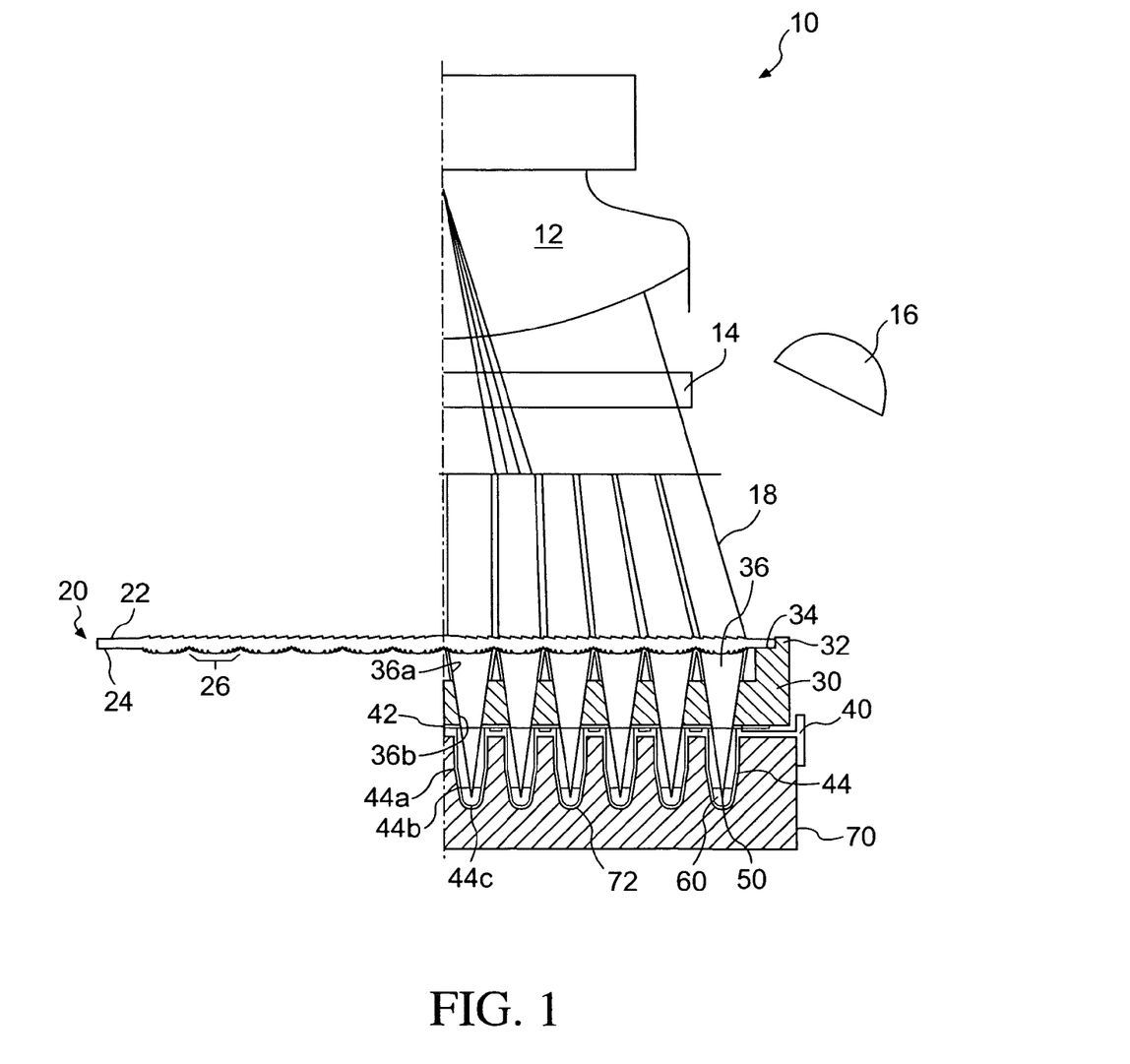
FIG. 1 is a partial section view of a biological testing device according to an exemplary embodiment of the invention.

In FIG. 1, a generally schematic view is shown that is representative of a biological testing device 10 according to an embodiment of the invention. For example, testing device 10 can be any type of device configured to perform nucleic acid amplification. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In one embodiment, the thermal cycling device performs real-time detection of the nucleic acid amplification of the samples during thermal cycling. Real-time detection systems are known in the art, as described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification.

In accordance with various embodiments, the testing device may include a light or radiation source. As embodied herein and shown in FIG. 1, the testing device includes a light source 16 for directing light onto a plurality of biological samples. The biological samples can be positioned in any type of known sample-receiving member. In the embodiment shown in FIG. 1, the samples 60 are located in sample wells 44 of a sample well tray 40. Light source 16 can be any conventional type of light source suitable for biological testing, such as a quartz bulb, a laser, (e.g. an argon ion laser), or an LED, for example. Light emitted from light source 16 can be aimed directly toward sample well tray 40, or light source 16 could be aimed at a beam splitter (not shown) that then can redirect at least a portion of the light toward sample well tray 40.

In accordance with various embodiments, biological testing device 10 includes an optical detection system. As embodied herein and shown in FIG. 1, an optical detection device 12 is positioned above the sample well tray 40. The optical detection system 12 is configured to detect and monitor the characteristics of the samples in the sample well tray 40 during the testing. Suitable structures and methods for the optical detection device 12 are well known in the art. The optical detection device can use any known structure or method. In one example, the optical detection device could include a CCD camera, in a manner known in the art. Likewise, the optical detection device can include any other type suitable for use with the thermal cycling device of the present invention.

In certain embodiments, a filter 14 can be provided for filtering the light reflected from the sample and allowing only a predetermined range of light waves to enter the optical detection device 12. Other elements known to be included in detecting devices can be included in testing device 10, such as a prism, a mirror, or a spectrograph, among others.

In accordance with various embodiments, a seal may be provided for the sample well tray. In one embodiment shown in FIG. 1, sample well tray 40 is covered by a film 42 for sealing the various sample wells 44 and for aiding in minimizing contamination of biological samples 60. Film 42 can be provided with an adhesive on the side facing sample well tray 40 to secure it in place. The film can be made out of any known material suitable for use with a sample well tray.

In accordance with various embodiments, the biological testing device can include a heated cover. In the embodiment shown in FIG. 1, a cover 30 is located above film 42. As shown in FIG. 1, cover 30 includes a lip 32 around its perimeter. Lip 32 can be continuous or it can be discontinuous. Lip 32 is raised above surface 34 onto which a lens array 20 may be placed. In combination, lip 32 and surface 34 can serve to locate and hold lens array 20 in a desired position in relation to cover 30. Cover 30 also includes a plurality of openings 36, with each opening being positioned over one of the sample wells 44 to allow light to pass through cover 30 and into biological samples 60 in the sample wells 44. As depicted in FIG. 1, openings 36 can taper from an upper edge 36a to a lower edge 36b. In certain embodiments, cover 30 can be heated to augment heating of biological samples 60 provided by a sample block 70. Acting as a heated cover, cover 30 can also serve a function to reduce condensation within the system.

In the embodiment shown, cover 30 rests on film 42, which in turn rests or is adhered to sample well tray 40. Sample well tray 40 can be any member utilized in biological testing to hold one or more samples. In the embodiment shown in FIG. 1, sample well tray 40 includes a plurality of sample wells 44 for holding biological samples 60. Sample wells 44 each comprise an upper portion 44a that has a substantially cylindrical shape and a tapered lower portion 44b that ends in a rounded bottom portion 44c. It is well understood that the sample wells may have any known size, shape, or configuration.

Biological testing device 10 can be configured for use with any type of sample well tray, including, for example, 96-well sample well trays, 384-well sample trays, and microcard sample trays. The size and shape of these sample well trays are well known in the art. Examples of 96-well sample well trays suitable for use in the present invention are described in WO00/25922 to Moring et al., the complete disclosure of which is hereby incorporated by reference for any purpose. Examples of sample well trays of the microcard type suitable for use in the present invention are described in WO01/28684 to Frye et al., the complete disclosure of which is hereby incorporated by reference for any purpose, WO97/36681 to Woudenberg et al., the complete disclosure of which is hereby incorporated by reference for any purpose, U.S. Pat. No. 6,514,750, assigned to the assignee of the present invention, the complete disclosure of which is hereby incorporated by reference for any purpose, and U.S. application Ser. No. 09/977,225, filed Oct. 16, 2001, assigned to the assignee of the present application, the complete disclosure of which is hereby incorporated by reference for any purpose. Sample well trays having any number of sample wells and sample well sizes may also be used with the thermal cycling device of the present invention. In the example shown in the figures, the volume of the sample wells can vary anywhere from about 0.01 µl to thousands of microliters (µl), with a volume between 10 to 500 µl being typical.

In accordance with various embodiments, the testing device can include a sample block. As embodied herein and shown in FIG. 1, sample well tray 40 can be configured to mount onto sample block 70. Sample block 70 can be any sample block known in the art that is used to receive a sample well tray and provide heating and/or cooling of biological samples 60. Sample block 70 can be machined or cast of a material suitable for conducting heat to sample tray 40 and can include a plurality of sample well openings 72 equal in number to a number of sample wells 44 of sample tray 40.

As mentioned above, lens array 20 can rest on, or be otherwise adjacent to, cover 30 and can perform the function of both focusing and collimating light emitted from and/or directed to samples 60. According to various aspects, lens array 20 can comprise a single element having at least two surfaces: a first surface 22 facing detection device 12 and a second surface 24 facing sample well tray 40. As used herein, "surface" is intended to broadly define a generally planar external portion of the lens that may include a plurality of sub-surfaces formed into the surface with the various sub-surfaces providing the desired overall lens characteristics.

According to various aspects, first surface 22 can comprise a Fresnel lens for collimating light, and second surface 24 can include a matrix 25 having a plurality of focusing lens portions or segments 26 equal to the number of sample wells 44. Each focusing lens portion or segment 26 is defined as the portion of surface 24 configured to focus light into an individual sample 60.

Figure 2:
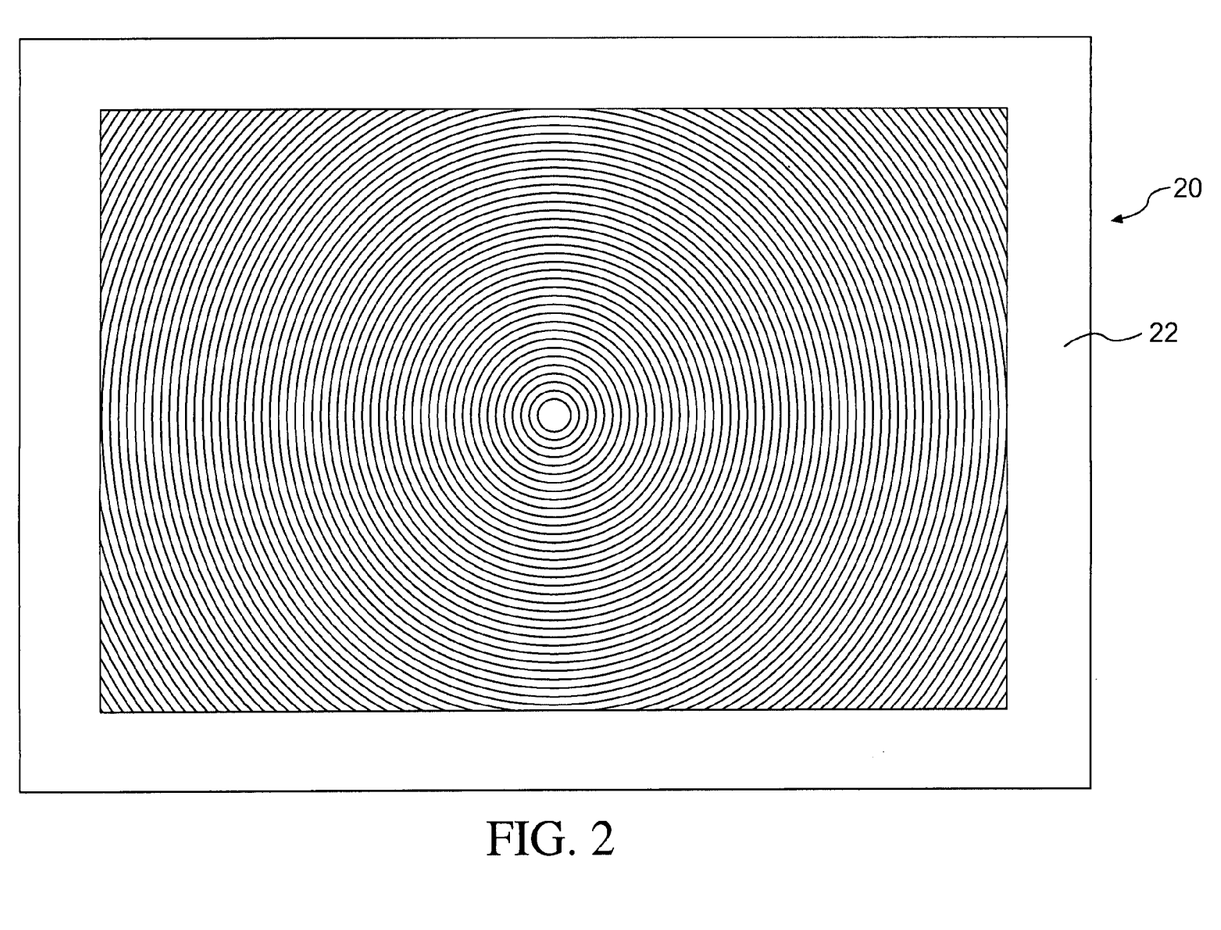
FIG. 2 is a plan view of a first side of a single-piece lens depicted in FIG. 1.

FIG. 2 shows the configuration of first surface 22. This configuration can be, for example, a Fresnel lens of the type manufactured by the Fresnel Technologies of Fort Worth Tex. There are at least two basic types of Fresnel lenses. The first has a constant pitch with increased depth toward the outer edges, and the second has a uniform depth. Either configuration could be used, but the uniform depth Fresnel lens is depicted in the embodiment shown in FIGS. 1-4.

Figure 3:
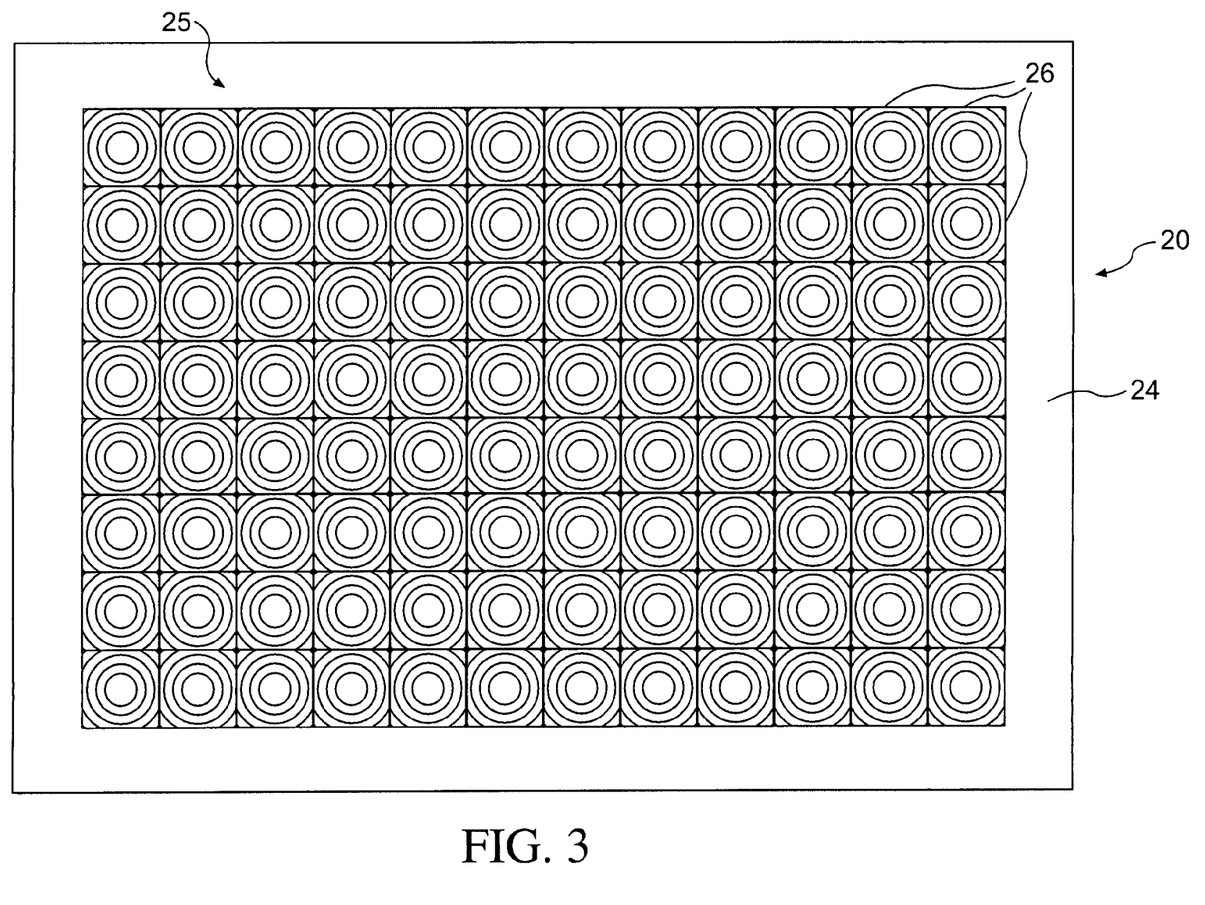
FIG. 3 is a plan view of a second side of the single-piece lens of FIG. 2.
Figure 4:
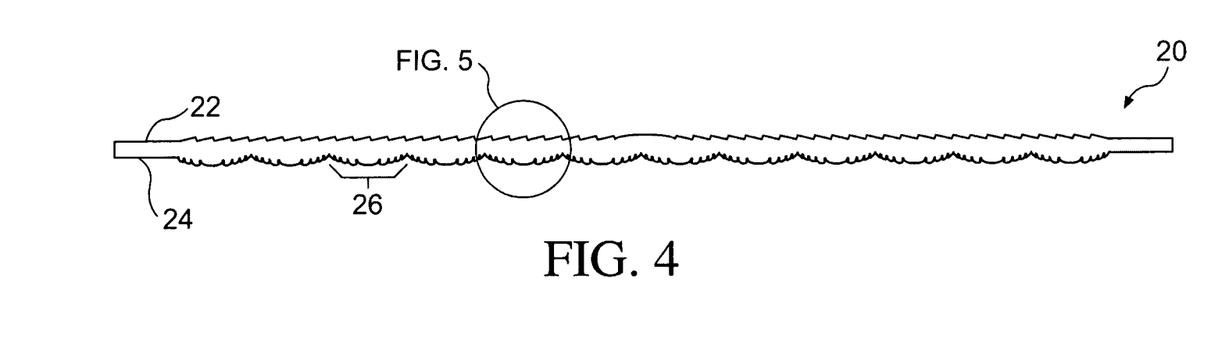
FIG. 4 is a section view of the single-piece lens of FIG. 2.

Each of the lens segments 26, shown in more detail in FIGS. 3 and 4, can comprise a hybrid achromatic lens such as, for example, a lens having refractive and diffractive features. According to various embodiments, each refractive element of the hybrid lens can comprise a spherical or aspherical surface having diffractive structures thereon.

In an exemplary operation, as can be seen in FIGS. 1-4, light emitted from light source 16 contacts first surface 22 of lens array 20. In the embodiment shown, first surface 22 can collimate light beams 18 so that the light is directed toward each of the rows or columns of sample wells 44 of sample well tray 40. Light beams 18 then pass through to a second surface 24 of lens array 20 which has formed on its surface a matrix 25 of focusing lenses (or focusing lens segments) 26 as shown in FIG. 3 for focusing light into each of biological samples 60 located in sample wells 44. Light beams 18 may have one or more wavelength selected to create luminescence by certain components of the samples 60 that a user wishes to identify. The wavelengths selected depend on the emission and absorption properties of the desired components. The luminescence from the samples 60 can pass through lens array 20 in a reverse direction of the light emitted from the light source 16. Lens array 20 can collect the reflected light and direct it toward detecting device 12.

It should be appreciated that according to various aspects, lens array 20 may regulate (e.g., collect, collimate, focus, and/or direct) light beams passing from the light source 16 toward the samples 60 and/or sample luminescence passing toward the detector 12.

Figure 5:
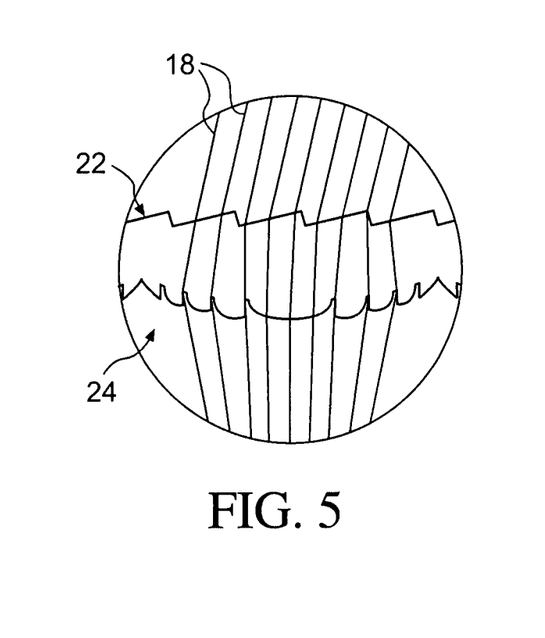
FIG. 5 is a close-up view of the circled portion of FIG. 4.

As seen in FIG. 5 in a close-up view of light passing through one of the focusing lens segments 26, light beams 18 pass through first side of lens 22 and are collimated. As beams 18 pass through the second surface 24, they are focused toward the desired sample location. As depicted, each lens segment 26 comprises a hybrid refractive/diffractive lens to accomplish the focusing, while reducing chromatic aberration. If the lens segments 26 have an aspheric surface, the lens array 20 may also reduce spherical aberration.

In the embodiment shown in FIGS. 1-4, lens array 20 integrates both the collimating function of side 22 and the focusing function of side 24 into a single, monolithic, lens array. First, as can be seen in FIG. 4, by forming the focusing lens segments 26 into the second surface 24 of lens array 20, focusing lens segment 26 may occupy a substantial portion of the area over its associated sample well 44. This expanded lens allows for a maximum amount of light to pass into each of the samples 60. In addition, focusing lens segments 26, being formed into the second surface 24, are fixed in relation to each other, thus minimizing the potential for movement between respective focusing lens segments.

Also, by integrating Fresnel lens side 22 and focusing lens side 24 into opposing surfaces of lens array 20, the potential for misalignment may be reduced or even eliminated between the collimating and focusing functions. Because Fresnel lens side 22 and focusing lens side 24 of lens array 20 are fixed in relation to each other, a correct alignment with respect to each other may be desirably maintained.

As described herein and shown in FIG. 1, heated cover 30 may also provide a mounting surface 34 for lens array 20 that may assist in maintaining a proper alignment between lens array 20 and sample well tray 40. Further enhancing this alignment, lens array 20 can optionally be fastened to heated cover 30 by any fastening means known in the art (e.g., a mechanical device such as clips, clamps, screws, adhesives, etc.) so as to further reduce movement and alignment problems between lens array 20 and heated cover 30.

In another aspect, lens array 20 may be configured so that one or more of lens segments 26 may provide light of a different intensity as compared to another of lens segments 26. According to some aspects, light source 16 may be a type of light source that emits light of focused intensity that is concentrated at a central area of lens array 20. As one moves toward the periphery of the lens assembly, the light emitted by light source 16 may be diminished. To compensate for this, one or more of focusing lens segments 26 may be configured in such a way as to substantially equalize the intensity of the light that is focused into each of the samples 60.

In certain embodiments, for example, the focusing lens segments 26 located near the center of lens array 20 could be molded in a fashion whereby the optics of the individual focusing lens segments could be varied so that they allow less light to pass through than focusing lens segments located at a periphery of lens array 20. For example, according to one aspect, the aperture of the focusing lens segments 26 may be limited. Any or all of focusing lens segments 26 could be altered in a similar fashion to correspond to varying intensities of light directed onto the grid of lens array 20. This could also be accomplished, for example, by masking a portion of selected focusing lens segments to reduce the amount of light that passes through them. The term "mask(ing)" as used herein is intended to mean reducing or completely inhibiting the light transmission capability of at least a portion of each of the focusing lens(es). This could be accomplished by applying a coating, for example paint, that would occlude at least a portion of the focusing lens segment. Masking could also include applying an adhesive material such as tape to a portion of the focusing lens segment for reducing the amount of light that passes through the lens. This masking could be done in various amounts throughout the lens matrix to achieve the desired intensity of light into each of the samples 60. For example, the masking may be performed cutting holes in a thin aluminum sheet, and then anodizing the sheet or painting it black.

Figure 6:
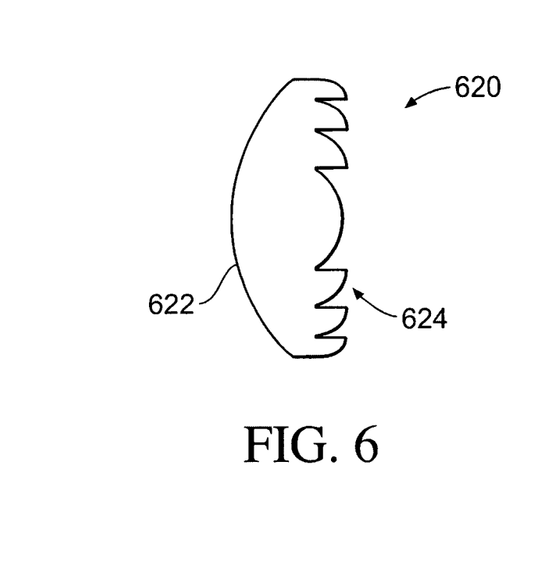
FIG. 6 is a section view of a exemplary single-piece lens in accordance with aspects of the invention.

Referring now to FIG. 6, in accordance with various aspects, the biological detection system 10 disclosed herein can comprise a hybrid achromatic lens 620 rather than lens array 20 described above. As shown, lens 620 can include a conventional refractive element on a first surface 622 and a diffractive element on an opposite second surface 624. Thus, lens 620 may be desirable in a detection system that does not require a Fresnel lens feature or in a detection system that includes a Fresnel lens element separate from the hybrid achromatic lens 620. The conventional refractive first surface 622 can comprise a spherical surface or an aspherical surface. Operationally, lens 620 functions similarly to the second surface 24 of lens array 20 in that light beams passing through the lens 620 are focused toward the desired sample location and chromatic aberrations can be minimized. An aspherical first surface 622 can also minimize spherical aberrations.

Lens array 20, 620 may be made by any suitable method. For example, it is contemplated that lens array 20, 620 could be manufactured by injection or compression molding. Lens array 20, 620 could be made of a non-fluorescing clear polycarbonate, for example. Testing devices using a heated cover, such as heated cover 30, often operate at temperatures approaching or even exceeding 80° C. For such high-temperature devices, a material such as Lexan is suitable for lens array 20. Devices operating at lower temperatures, for example at or near 60° C., may include a lens made of any number of materials such as acrylics, styrenes, polyethylenes, polycarbonates, polypropylenes, or any other transparent plastic that may be suitable. Other materials, such as glass, may also be contemplated that would provide the same or similar characteristics as the ones included herein.

Although lens array 20 is shown in a 12×8 grid configuration comprising 96 focusing lens segments, it is to be understood that this lens configuration could be modified into substantially any configuration to correspond with various sample well tray configurations or shapes. For example, lens array 20, 620 could have 4, 8, 12, 24, 96, 384, or 1536 focusing lens segments. Lens array 20, 620 could also be formed in various shapes other than a rectangle so as to conform to a shape of a sample well tray.

FIGS. 1-4 show the lens array 20 in combination with a heated cover 30 and sample well tray 40 with a plurality of sample wells 44. In certain embodiments, lens array 20, 620 can be used with other sample testing devices that may or may not have a heated cover. For example, FIG. 7 shows the lens array 20 in use with a sample testing device that does not have a heated cover.

Figure 7:
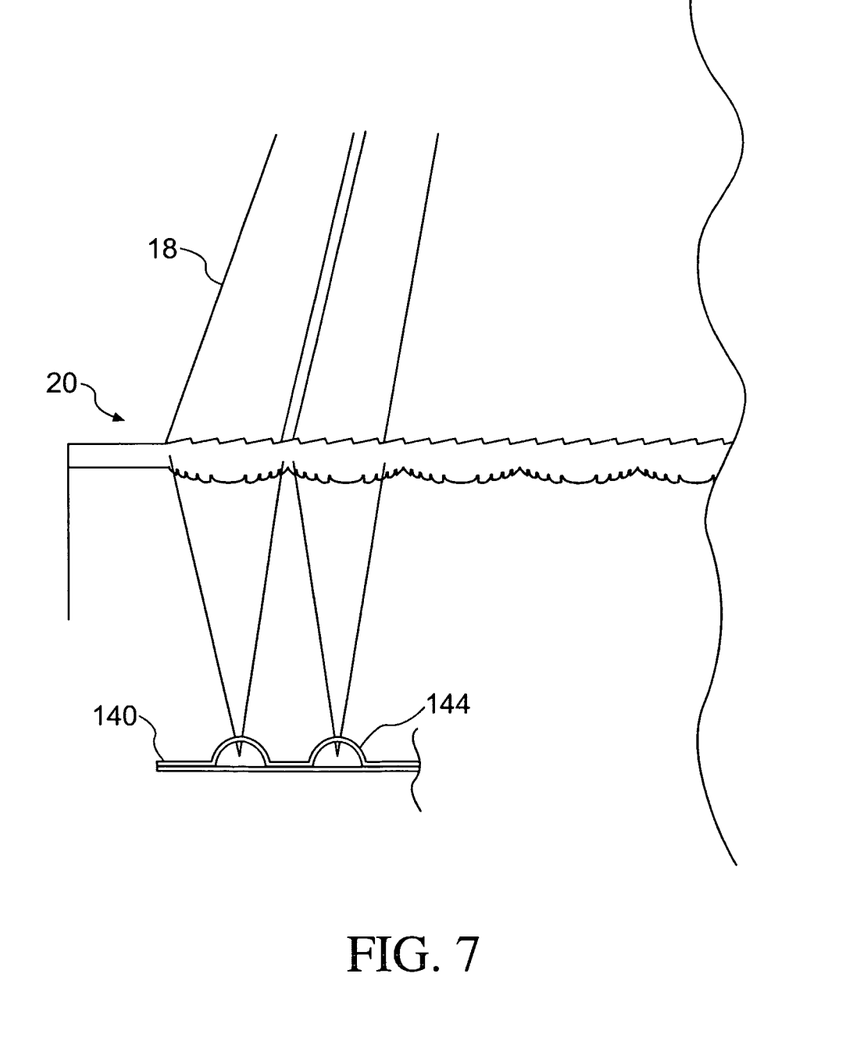
FIG. 7 is a partial section of the lens of FIG. 1 in combination with a microcard sample tray.

In FIG. 7, lens array 20 is used in combination with a microcard sample tray 140. As discussed above, microcard sample trays are known to those skilled in the art. In the embodiment shown in FIG. 7, microcard sample tray 140 includes a plurality of sample wells or chambers 144 configured to contain a sample for testing. Chambers 144 may align with a matrix of lenses in a fashion similar to the sample well tray 40 of FIG. 1. Microcard sample tray 140 can have any of the various configurations, sizes and shapes known in the art. In the embodiment shown in FIG. 5, the microcard sample tray is used without a heated cover. Microcard sample tray 140 may also be used with a heated cover.

It should be appreciated that the lens array 20, 620, including the lens segments 26 with diffractive and/or refractive features are illustrative only and are not intended to be drawn to scale.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a biological" includes two or more different biological samples. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the structure. Thus, it should be understood that the invention is not limited to the examples discussed in the specification. Rather, the present invention is intended to cover modifications and variations.

What is claimed is:

1. An optical detection system, comprising:
   a light source configured to illuminate at least one of a plurality of biological samples;
   a light detection device configured to detect luminescence from at least one of a plurality of biological samples;
   a single-piece lens having first and second surfaces formed on the lens, the second surface facing a direction opposite to that of the first surface, the first surface collimating light from the light source and the second surface comprising a plurality of diffractive elements configured to receive transmitted light from the first surface and produce a plurality of focal spots from light received from a common light source, at least one of the diffractive elements comprising at least one of a diffraction grating, a surface-relief diffractive lens, or a holographic optical element; and
   a sample block assembly configured to receive a sample well tray, the sample well tray being configured to contain the plurality of biological samples, the sample block assembly including a heated cover configured to receive the lens.

2. The optical detection system of claim 1, wherein the first surface comprises a spherical refractive surface.

3. The optical detection system of claim 1, wherein the lens is made of a material chosen from one of a glass and a plastic.

4. The optical detection system of claim 1, wherein the light source is chosen from at least one of a laser, an electroluminescent light source, an chemiluminescent light source, an electrochemiluminescent light source, an incandescent light source, a fluorescent light source, an arc lamp, and a light emitting diode.

5. The optical detection system of claim 1, wherein the light source is chosen from a gas laser, a solid state laser, a fiber optical laser, and an organic based laser.

6. The optical detection system of claim 1, wherein each focusing lens portion-comprises at least one refractive feature, the at least one refractive feature comprising an aspheric refractive surface configured to reduce a spherical aberration of at least one of the light from the light source or the luminescence from the target.

7. The optical detection system of claim 1, wherein the plurality of diffractive elements corresponds to the plurality of biological samples.

8. The optical detection system of claim 1, wherein the plurality of diffractive elements comprises 4, 8, 12, 24, 48, 96, 384, or 1,536 focusing lens portions.

9. The optical detection system of claim 1, further comprising a sample block assembly configured to receive a sample well tray, the sample well tray being configured to contain the plurality of biological samples, the sample block assembly including a heated cover configured to receive the lens.

10. The optical detection system of claim 1, wherein the first lens surface comprises a Fresnel lens.

11. The optical detection system of claim 1, wherein the light source is configured to provide light of a non-uniform intensity across the first surface, and the second surface is configured to provide light at approximately uniform intensity to each of the plurality of biological samples.

12. The optical detection system of claim 1, wherein the plurality of diffractive elements comprises distinct portions of the second surface, the distinct portions configured to direct light toward a respective one of a plurality of biological samples.

13. The optical detection system of claim 1, further comprising a sample holder comprising a plurality of sample chambers configured to contain corresponding biological samples, the plurality of diffractive elements comprising distinct portions of the second surface, each distinct portions focusing light toward a respective one of the sample chambers.

14. The optical detection system of claim 1, wherein the plurality of diffractive elements are arranged to form in a two-dimension of focusing elements.

15. The optical detection system of claim 1, wherein the plurality of diffractive elements are arranged to form a rectangular area.

16. The optical detection system of claim 1, wherein the diffractive elements is configured to reduce a chromatic aberration.

* * * * *